US011045489B2

(12) United States Patent
Avigad et al.

(10) Patent No.: US 11,045,489 B2
(45) Date of Patent: Jun. 29, 2021

(54) PROGNOSTIC METHODS AND SYSTEMS OF TREATMENT FOR ACUTE LYMPHOBLASTIC LEUKEMIA

(71) Applicant: MOR RESEARCH APPLICATIONS LTD., Tel Aviv (IL)

(72) Inventors: Smadar Avigad, Tel Aviv (IL); Isaac Yaniv, Tel Aviv (IL); Keren Shichrur, Tel Aviv (IL)

(73) Assignee: MOR RESEARCH APPLICATIONS LTD., Tel Aviv (IL)

( * ) Notice: Subject to any disclaimer, the term of this patent is extended or adjusted under 35 U.S.C. 154(b) by 0 days.

(21) Appl. No.: 16/567,233

(22) Filed: Sep. 11, 2019

(65) Prior Publication Data
US 2019/0388457 A1    Dec. 26, 2019

Related U.S. Application Data

(63) Continuation of application No. 15/500,104, filed as application No. PCT/IL2015/050790 on Jul. 30, 2015, now abandoned.

(60) Provisional application No. 62/030,629, filed on Jul. 30, 2014.

(51) Int. Cl.
| | | |
|---|---|---|
| C12Q 1/68 | (2018.01) | |
| A61K 31/7105 | (2006.01) | |
| G01N 33/574 | (2006.01) | |
| C12N 15/113 | (2010.01) | |
| C12Q 1/6886 | (2018.01) | |
| A61K 31/4025 | (2006.01) | |
| A61K 39/395 | (2006.01) | |

(52) U.S. Cl.
CPC ...... *A61K 31/7105* (2013.01); *A61K 31/4025* (2013.01); *A61K 39/3955* (2013.01); *C12N 15/1137* (2013.01); *C12Q 1/6886* (2013.01); *G01N 33/57426* (2013.01); *C12N 2310/141* (2013.01); *C12Q 2600/106* (2013.01); *C12Q 2600/118* (2013.01); *C12Q 2600/158* (2013.01); *C12Q 2600/178* (2013.01); *G01N 2800/54* (2013.01)

(58) Field of Classification Search
None
See application file for complete search history.

(56) References Cited

U.S. PATENT DOCUMENTS 10,557,173 B2 *    2/2020    Avigad ................. C12Q 1/6886

FOREIGN PATENT DOCUMENTS

| CN | 102209729 | 10/2011 |
|----|-----------|---------|
| CN | 102859361 | 1/2013 |
| CN | 102925575 | 2/2013 |
| CN | 103627810 | 3/2014 |
| WO | 2012042516 | 4/2012 |
| WO | 2016016898 | 2/2016 |

OTHER PUBLICATIONS

Strausberg et al, in Microarrays and Cancer Research, 2002, Warrington etal (eds.), Eaton Publishing, Westborough, MA, p. xi-xvi.*
Notterman et al, in Microarrays and Cancer Research, 2002, Warrington etal (eds.), Eaton Publishing, Westborough, MA, pp. 81-111.*
Burnham, Bryan R, Fundamental Statistics for the Behavioral Sciences (v.2.1) Chapter 10 (Available at https://sites.google.com/site/fundamentalstatistics/chapter-10), 13 pages.
Teachy et al., British Journal of Haematology, 2013, 162, 606-620.
Wang et al. Blood Cells Mol Dis. Mar. 15, 2010; 44(3), 191.
Wenying Li, et al, "Oncomirnas and Tumor Suppressors in Microvesicles From Four Types of Cancer" Blood 2013 122:4900.
Mosakhani, "MicroRNAs as Predictive and Prognostic Biomarkers in Human Neoplasia: With Specific Focus on Colorectal Cancer, Giant Cell Tumor of Bone, and Leukemias" University of Helsinki Thesis, 2013, available at https://helda.helsinki.fi/bitstream/handle/10138/38570/MicroRNA.pdf?sequence=1 (82 pages).
Matheny et al "Next-generation NAMPT inhibitors identified by sequential high throughput phenotypic chemical and functional genomic screens" Chem Biol. Nov. 21, 2013; 20(11), 23 pages.
Schotte et al, "Identification of new microRNA genes and aberrant microRNA profiles in childhood acute lymphoblastic leukemia" Leukemia (2009) 23, 313-322.
Chen, Xiaomei, et al. "Analysis of Microvesicle Microrna Expression Profiles and Their Functional Roles in All Subtypes." 53rd ASH Annual Meeting and Exposition, Oct. 12, 2020 retrieved from the Internet on: Nov. 16, 2015; URL: https://ash.confex.com/ash/2011/webprograom/Paper37549.html Dec. 10, 2011.

(Continued)

*Primary Examiner* — James Matinell
(74) *Attorney, Agent, or Firm* — JMB Davis Ben-David

(57) ABSTRACT

Described herein are methods for determining the prognosis of a patient diagnosed with Acute Lymphoblastic Leukemia (ALL), and particularly determining the risk of disease relapse following standard treatment. Also described are systems of treatment that are directed by a health care provider, and which include the described prognostic methods and the treatments recommended for patients determined to have a specific relapse risk.

15 Claims, 10 Drawing Sheets

Specification includes a Sequence Listing.

(56) References Cited

OTHER PUBLICATIONS

Li X et al, "Repression of tumor suppressor miR-451 is essential for NOTCH1-induced oncogenesis in T-ALL", The Journal of Experimental Medicine, (Apr. 11, 2011), vol. 208, No. 4, doi:10.1084/JEM.20102384, ISSN 0022-1007, pp. 663-675.
Ubaldina Galli et al, "Medicinal Chemistry of Nicotinamide Phosphoribosyltransferase (NAMPT) Inhibitors", Journal of Medicinal Chemistry, (Aug. 22, 2013), vol. 56, No. 16, doi:10.1021/jm4001049, ISSN 0022-2623, pp. 6279-6296.

* cited by examiner

SEQUENCE LISTING

<160> NUMBER OF SEQ ID NOS: 8

<210> SEQ ID NO 1
<211> LENGTH: 21
<212> TYPE: RNA
<213> ORGANISM: Homo sapiens

<400> SEQUENCE: 1
ucgaggagcu cacagucuag u                                               21

<210> SEQ ID NO 2
<211> LENGTH: 22
<212> TYPE: RNA
<213> ORGANISM: Homo sapiens

<400> SEQUENCE: 2
aaaccguuac cauuacugag uu                                              22

<210> SEQ ID NO 3
<211> LENGTH: 17
<212> TYPE: RNA
<213> ORGANISM: Homo sapiens

<400> SEQUENCE: 3
uggauuuuug gaucagg                                                    17

<210> SEQ ID NO 4
<211> LENGTH: 29
<212> TYPE: RNA
<213> ORGANISM: Artificial Sequence
<220> FEATURE:
<223> OTHER INFORMATION: Sythetic oligonucleotide

<400> SEQUENCE: 4
uggauuuuug gaucaccuga uccaaaaau                                       29

<210> SEQ ID NO 5
<211> LENGTH: 11
<212> TYPE: RNA
<213> ORGANISM: Artificial Sequence
<220> FEATURE:
<223> OTHER INFORMATION: Sythetic oligonucleotide

<400> SEQUENCE: 5
ucccugaucc a                                                          11

<210> SEQ ID NO 6
<211> LENGTH: 50
<212> TYPE: DNA
<213> ORGANISM: Artificial Sequence
<220> FEATURE:
<223> OTHER INFORMATION: Sythetic oligonucleotide

<400> SEQUENCE: 6
gtcgtatcca gtgcagggtc cgaggtattc gcactggata cgacactaga                50

<210> SEQ ID NO 7
<211> LENGTH: 50
<212> TYPE: DNA
<213> ORGANISM: Artificial Sequence
<220> FEATURE:
<223> OTHER INFORMATION: Sythetic oligonucleotide

<400> SEQUENCE: 7
gtcgtatcca gtgcagggtc cgaggtattc gcactggata cgacaactca                50

```
<210> SEQ ID NO 8
<211> LENGTH: 50
<212> TYPE: DNA
<213> ORGANISM: Artificial Sequence
<220> FEATURE:
<223> OTHER INFORMATION: Sythetic oligonucleotide

<400> SEQUENCE: 8
gtcgtatcca gtgcagggtc cgaggtattc gcactggata cgactccctg            50
```

PROGNOSTIC METHODS AND SYSTEMS OF TREATMENT FOR ACUTE LYMPHOBLASTIC LEUKEMIA

CROSS REFERENCE TO RELATED APPLICATIONS

This is a Continuation of U.S. patent application Ser. No. 15/500,104, filed Jan. 30, 2017, which is the US National Stage of International Patent Application No. PCT/IL2015/050790, filed Jul. 30, 2015, and which in turn claimed the benefit of U.S. Provisional Patent Application No. 62/030,629, filed Jul. 30, 2014. The contents of the foregoing patent applications are incorporated by reference in their entirety.

FIELD

Provided herein are methods for determining the prognosis of a patient diagnosed with Acute Lymphoblastic Leukemia (ALL), and particularly determining the risk of disease relapse following standard treatment. Further provided herein are systems of treatment that are directed by a health care provider, and which include the described prognostic methods and the treatments recommended for patients determined to have a specific relapse risk.

BACKGROUND

Leukemia is a cancer of the blood or bone marrow characterized by an abnormal increase of blood cells, usually leukocytes. Leukemia is clinically and pathologically subdivided into a variety of large groups, including its acute and chronic forms. Acute leukemia is characterized by the rapid increase of immature blood cells. This crowding makes the bone marrow unable to produce healthy blood cells Immediate treatment is required in acute leukemia due to the rapid progression and accumulation of the malignant cells, which then spill over into the bloodstream and spread to other organs of the body. Acute forms of leukemia are the most common forms of leukemia in children, of which, acute lymphoblastic leukemia (ALL) is the most prevalent.

Current treatments for ALL are guided by patient assessment and classification into a particular risk group. Examples of such classifications include the Berlin-Frankfurt-Munster (BFM), the Children's Oncology Group (COG) (Schrappe, Ann Hematol. (2004); 83: S121-3; Vrooman L M et al., Curr Opin Pediatr. (2009); 21(1):1-8), UKALL, from the United Kingdom, the Chinese Children's Leukemia Group (CCLG), and the Dana-Farber Cancer Institute ALL Consortium (DFCI). In the classifications, patients are classified inter alia on white blood cell count, chromosomal rearrangement, and responsiveness to prednisone treatment at day 8 following treatment initiation. Classification into a particular group will determine how aggressively a patient is treated in order to provide effective treatment and to reduce the possibility of disease relapse.

While current methods of diagnosis and treatment have improved the cure rate up to 80-90%, certain children are still over- or under-treated (Schrappe M et al., Leukemia. (2010); 24: 253-254; Pui C H and Evans W E, N. Engl. J. Med. (2006); 354: 166-178; Bhojwani D et al., Clin. Lymphoma. Myeloma. (2009); 3:S222-230]. Moreover, current prognostic methods only determine a patient's risk of relapse months after initial diagnosis. Thus, a continuing need exists for both better ALL prognostic methods that can classify a patient closer to the initiation of treatment, and systems of treatment that are prescribed by the determined risk of relapse.

SUMMARY

Provided herein are methods of prognosis of acute lymphoblastic leukemia (ALL) in a subject, by determining the expression level of miR-1290 in a sample from the subject (such as a bone marrow sample); and comparing the miR-1290 expression level in the subject with control expression of miR-1290, wherein a significant increase in miR-1290 expression in the subject in comparison to the control expression indicates that the subject has an increased risk of ALL relapse; and wherein a significant decrease in miR-1290 expression in the subject in comparison to the control expression indicates that the subject has a reduced risk of ALL relapse.

Also provided are methods of prognosis of acute lymphoblastic leukemia (ALL) in a subject, by determining the expression level of miR-1290, and at least one of miR-151-5p and miR-451 in a sample from the subject (such as a bone marrow sample); and comparing the determined expression of miR-1290, and miR-151-5p and/or miR-451 with control expression of miR-1290, and miR-151-5p and/or miR-451, wherein a significant increase in miR-1290 expression in the subject in comparison to the control miR-1290 expression, combined with a significant decrease in expression of the at least one of miR-151-5p and miR-451 in comparison to the control expression of miR-151-5p and/or miR-451, indicates that the subject has an increased risk of ALL relapse; and wherein a significant decrease in miR-1290 expression in the subject in comparison to the control expression, combined with a significant increase in expression of the at least one of miR-151-5p and miR-451 in comparison to the control expression of miR-151-5p and/or miR-451, indicates that the subject has a reduced risk of ALL relapse.

Further described herein are systems of ALL treatment that include determining the expression level of miR-1290 in a sample from the subject (such as a bone marrow sample); comparing the miR-1290 expression level in the subject with control expression of miR-1290, wherein a significant increase in miR-1290 expression in the subject in comparison to the control expression indicates that the subject has an increased risk of ALL relapse, and requires treatment appropriate for a subject with an increased risk of ALL relapse; and administering to the patient an ALL treatment designated as appropriate for a patient with an increased risk of ALL relapse.

An additionally described system of ALL treatment includes determining the expression level of miR-1290 and at least one of miR-151-5p and miR-451 in a sample from a subject (such as a bone marrow sample); and comparing the determined expression of miR-1290, and miR-151-5p and/or miR-451 with control expression of miR-1290, and miR-151-5p and/or miR-451, wherein a significant increase in miR-1290 expression in the subject in comparison to the control miR-1290 expression, combined with a significant decrease in expression of the at least one of miR-151-5p and miR-451 in comparison to the control expression of miR-151-5p and/or miR-451, indicates that the subject has an increased risk of ALL relapse, and requires treatment appropriate for a subject with an increased risk of ALL relapse; and administering to the patient an ALL treatment designated as appropriate for a patient with an increased risk of ALL relapse.

The foregoing and other objects, features, and advantages will become more apparent from the following detailed description, which proceeds with reference to the accompanying figures.

BRIEF DESCRIPTION OF THE DRAWINGS

FIG. 4A: expression analysis of hsa-miR-451 measured by quantitative Real Time-PCR (qRT-PCR). Expression of hsa-miR-451 in Nalm-6 cells transfected with miR-451 24 hr after transfection, 5 day and 10 days after transfection, and in cells transfected with scrambled miRNA as negative control (Control). FIG. 4B: comparison of tumor size in female NOD/SCID mice transplanted with Nalm-6 cells transfected with miR-451, Nalm-6 transfected with cells transfected with scrambled miRNA as negative control (Control), for 31 days after s.c. injection of cells. FIG. 4C: mean tumor weight in NOD/SCID mice transplanted with Nalm-6 cells transfected with miR-451, Nalm-6 cells transfected with scrambled miRNA as Negative control (Control) at the end of the experiment. bars, SE. *, P<0.05.

FIG. 5A: expression analysis of NAMPT measured by FACS in NALM-6 cell line expressing miR-451 mimic, inhibitor and scrambled control. FIG. 5B: Luciferase reporter assay validating the direct interaction of miR-451 with the 3'UTR of NAMPT. bars, SE. *, P<0.05.

FIG. 6A: expression analysis of NAMPT measured by quantitative reverse transcription-PCR (RT-PCR) in NALM-6 cell line treated with 50 ng/ml TPA for 24 hours. FIG. 6B: $NAD^+$ assay in cells treated with 50 nM TPA for 24 hours. bars, SE.

FIG. 7A: NAD levels were measured using NAD assay in cells treated with FK866 for 1, 3 and 6 hours. FIG. 7B: Apoptosis was measured with apoptosis kit in cells treated with the NAMPT inhibitor, FK866. bars, SE. *, P<0.05.

BRIEF DESCRIPTION OF THE DESCRIBED SEQUENCES

Figure 1:
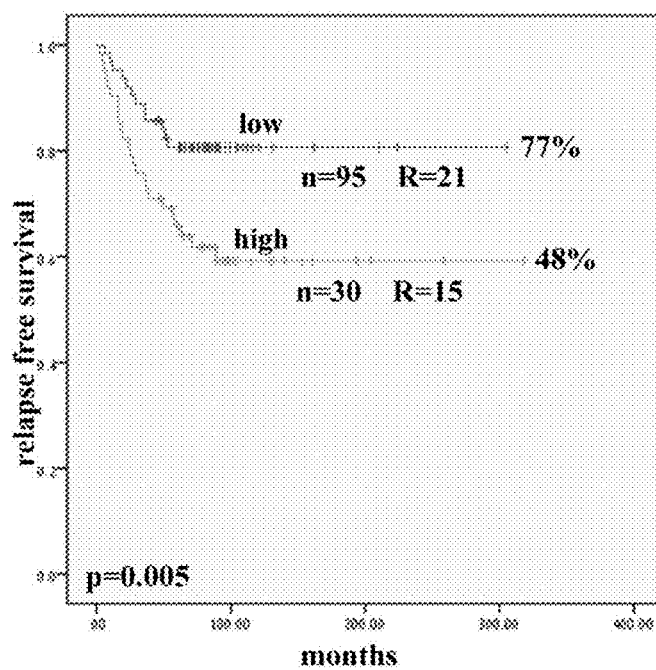
FIG. 1 is a Kaplan Meier estimation of Relapse Free Survival (RFS) in a cohort of 125 ALL patients. In the plot, the line representing high or low expression of miR-1290 is accordingly indicated.

The nucleic acid sequences provided herewith are shown using standard letter abbreviations for nucleotide bases as defined in 37 C.F.R. 1.822. Only one strand of each nucleic acid sequence is shown, but the complementary strand is understood as included by any reference to the displayed strand. The Sequence Listing is submitted as an ASCII text file named 3044_3_SEQLIST.txt, created Jul. 30, 2015, about 1.48 KB, which is incorporated by reference herein. In the accompanying sequence listing:

SEQ ID NO: 1 is the nucleotide sequence of miR-151-5p.
SEQ ID NO: 2 is the nucleotide sequence of miR-451.
SEQ ID NO: 3 is the nucleotide sequence of miR-1290.
SEQ ID NO: 4 is the nucleotide sequence of a mIR-1290 mimic
SEQ ID NO: 5 is the nucleotide sequence of a mIR-1290 inhibitor.
SEQ ID NO: 6 is the nucleotide sequence of a stem loop reverse transcription DNA primer for miR-151-5p.
SEQ ID NO: 7 is the nucleotide sequence of a stem loop reverse transcription DNA primer for miR-451.
SEQ ID NO: 8 is the nucleotide sequence of a stem loop reverse transcription DNA primer for miR-1290.

DETAILED DESCRIPTION

I. Abbreviations

ALL Acute lymphoblastic leukemia
MRD Minimal residual disease

II. Terms

Unless otherwise noted, technical terms are used according to conventional usage, which for example can be found in Benjamin Lewin, *Genes V*, published by Oxford University Press, 1994 (ISBN 0-19-854287-9); Kendrew et al. (eds.), The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example." In case of conflict, the present specification, including explanations of terms, will control. In addition, all the materials, methods, and examples are illustrative and not intended to be limiting.

Abnormal: Deviation from normal characteristics. Normal characteristics can be found in a control, a standard for a population, etc. For instance, where the abnormal condition is a disease condition, such as ALL, a few appropriate sources of normal characteristics might include an individual who is not suffering from the disease, or a population who did not experience a particular prognosis outcome of the disease, such as ALL relapse. Similarly, abnormal may refer to a condition that is associated with a disease or disease relapse. The term "associated with" includes an increased risk of developing the disease or a relapse thereof. For instance, a certain abnormality (such as an abnormality in expression of a miRNA) can be described as being associated with the biological condition of ALL relapse. Controls or standards appropriate for comparison to a sample, for the determination of abnormality, such as in the determination of an expression cutoff value, include samples believed to be normal as well as laboratory-determined values, even though such values are possibly arbitrarily set, and keeping in mind that such values may vary from laboratory to laboratory. Laboratory standards and values may be set based on a known or determined population value and may be supplied in the format of a graph or table that permits easy comparison of measured, experimentally determined values.

Altered expression: Expression of a biological molecule (for example, a miRNA) in a subject or biological sample from a subject that deviates from expression if the same biological molecule in a subject or biological sample from a subject having normal or unaltered characteristics for the biological condition associated with the molecule. Normal expression can be found in a control, a standard for a population, etc. Altered expression of a biological molecule may be associated with a disease or condition thereof, such as ALL relapse.

Amplification: When used in reference to a nucleic acid, any technique that increases the number of copies of a nucleic acid molecule in a sample or specimen. An example of amplification is the polymerase chain reaction (in all of its forms), in which a biological sample collected from a subject is contacted with a pair of oligonucleotide primers, under conditions that allow for the hybridization of the primers to nucleic acid template in the sample. The primers are extended under suitable conditions, dissociated from the template, and then re-annealed, extended, and dissociated to amplify the number of copies of the nucleic acid. The product of in vitro amplification can be characterized by electrophoresis, restriction endonuclease cleavage patterns, oligonucleotide hybridization or ligation, and/or nucleic acid sequencing, using standard techniques. Other examples of in vitro amplification techniques include strand displacement amplification (see U.S. Pat. No. 5,744,311); transcription-free isothermal amplification (see U.S. Pat. No. 6,033,881); repair chain reaction amplification (see WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

Biological Sample: Any sample that may be obtained directly or indirectly from an organism, including whole blood, plasma, serum, tears, mucus, saliva, urine, pleural fluid, spinal fluid, gastric fluid, sweat, semen, vaginal secretion, sputum, fluid from ulcers and/or other surface eruptions, blisters, abscesses, tissues, cells (such as, fibroblasts, peripheral blood mononuclear cells, or muscle cells), organs, and/or extracts of tissues, cells (such as, fibroblasts, peripheral blood mononuclear cells, or muscle cells), or organs. A sample is collected or obtained using methods well known to those skilled in the art.

cDNA (complementary DNA): A piece of DNA lacking internal, non-coding segments (introns) and transcriptional regulatory sequences. cDNA can also contain untranslated regions (UTRs), such as those that are responsible for translational control in the corresponding RNA molecule. cDNA is synthesized in the laboratory by reverse transcription from RNA extracted from cells.

Chemotherapeutic agent: An agent with therapeutic usefulness in the treatment of diseases characterized by abnormal cell growth or hyperplasia. Such diseases include cancer, autoimmune disease as well as diseases characterized by hyperplastic growth such as psoriasis. One of skill in the art can readily identify a chemotherapeutic agent (for instance, see Slapak and Kufe, *Principles of Cancer Therapy*, Chapter 86 in *Harrison's Principles of Internal Medicine*, 14th edition; Perry et al., *Chemotherapy*, Ch. 17 in Abeloff, *Clinical Oncology* $2^{nd}$ed., © 2000 Churchill Livingstone, Inc; Baltzer L, Berkery R (eds): *Oncology Pocket Guide to Chemotherapy*, 2nd ed. St. Louis, Mosby-Year Book, 1995; Fischer D S, Knobf M F, Durivage H J (eds): *The Cancer Chemotherapy Handbook*, 4th ed. St. Louis, Mosby-Year Book, 1993). Examples of chemotherapeutic agents include ICL-inducing agents, such as melphalan (Alkeran™), cyclophosphamide (Cytoxan™), cisplatin (Platinol™) and busulfan (Busilvex™, Myleran™).

Control: A reference standard. A control can be a known value indicative of basal expression of a diagnostic molecule such as miR-1290. In particular examples a control sample is taken from a subject that is known not to have a disease or condition, including ALL patients who did or did not experience disease relapse. In other examples a control is taken from the subject being diagnosed, but at an earlier time point, either before disease onset or prior to or at an earlier time point in disease treatment. A difference between a test sample and a control can be an increase or conversely a decrease. The difference can be a qualitative difference or a quantitative difference, for example a statistically significant difference. In some examples, a difference is an increase or decrease, relative to a control, of at least about 10%, such as at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 500%, or greater than 500%. In a further particular example, the control expression value of an miRNA of interest was set as the upper third quartile or median of a group of ALL patients before starting disease treatment.

Detect: To determine if an agent (such as a signal or particular nucleic acid probe) is present or absent. In some examples, this can further include quantification.

Determining expression of a gene product: Detection of a level of expression (for example a nucleic acid) in either a qualitative or a quantitative manner. In one example, it is the detection of a miRNA, as described herein.

Diagnosis: The process of identifying a disease or a predisposition to developing a disease or condition, for example ALL or its relapse, by its signs, symptoms, and results of various tests and methods, for example the methods disclosed herein. The conclusion reached through that process is also called "a diagnosis." The term "predisposition" refers to an effect of a factor or factors that render a subject susceptible to or at risk for a condition, disease, or disorder, such as ALL or its relapse. In the disclosed methods, specific miRNA expression determination to identify a subject predisposed to (or at an increased risk for) ALL relapse.

Increased risk: As used herein "increased risk" of ALL relapse refers to an increase in the statistical probability of an ALL patient relapsing relative to the general population, following standard disease treatment. As described herein, the risk of a subject determined to have an increased risk of ALL relapse may have a high risk or intermediate risk, both of which are an increased risk in comparison to "standard risk".

Label: A detectable compound or composition that is conjugated directly or indirectly to another molecule to facilitate detection of that molecule. Specific, non-limiting examples of labels include radioactive isotopes, enzyme substrates, co-factors, ligands, chemiluminescent or fluorescent agents, haptens, and enzymes.

Mammal: This term includes both human and non-human mammals. Similarly, the term subject includes both human and veterinary subjects.

MicroRNA (miRNA): Short, single-stranded RNA molecule of 18-24 nucleotides long. Endogenously produced in cells from longer precursor molecules of transcribed non-coding DNA, miRNAs can inhibit translation, or can direct cleavage of target mRNAs through complementary or near-complementary hybridization to a target nucleic acid (Boyd, *Lab Invest.,* 88:569-578, 2008). As used herein, a "microRNA sequence" includes both mature miRNA sequences and precursor sequences such as pri-miRNA, pre-miRNA, and the like.

Oligonucleotide: A plurality of joined nucleotides, between about 6 and about 300 nucleotides in length. An oligonucleotide analog refers to a subclass of oligonucleotides that contain moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include peptide nucleic acid (PNA) molecules. Particular oligonucleotides and oligonucleotide analogs can include linear sequences up to about 200 nucleotides in length, for example a sequence (such as DNA or RNA) that is at least 6 bases, for example at least 8, 10, 15, 20, 25, 30, 35, 40, 45, 50, 100 or even 200 bases long, or from about 6 to about 50 bases, for example about 10-25 bases, such as 12, 15 or 20 bases.

Predicted to benefit from: Indicates that a subject would likely benefit from a particular treatment. For example, current treatments of ALL relapse high-risk patients include anthracycline therapy. As used herein, a patient determined to have a high risk of ALL relapse would be predicted to benefit from anthracycline treatment.

Probes and primers: Nucleic acid probes and primers can be readily prepared based on the nucleic acid molecules provided in this invention. A probe comprises an isolated nucleic acid attached to a detectable label or reporter molecule. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, for example, in Sambrook et al. (ed.), *Molecular Cloning: A Laboratory Manual,* $2^{nd}$ ed., vol. 1-3, Cold Spring Harbor Laboratory Press, Cold Spring Harbor, N.Y., 1989 and Ausubel et al. *Short Protocols in Molecular Biology,* $4^{th}$ ed., John Wiley & Sons, Inc., 1999.

Primers are short nucleic acid molecules, preferably DNA oligonucleotides 10 nucleotides or more in length. More preferably, longer DNA oligonucleotides can be about 15, 17, 20, or 23 nucleotides or more in length. Primers can be annealed to a complementary target DNA strand by nucleic acid hybridization to form a hybrid between the primer and the target DNA strand, and then the primer extended along the target DNA strand by a DNA polymerase enzyme. Primer pairs can be used for amplification of a nucleic acid sequence, e.g., by the PCR or other nucleic-acid amplification methods known in the art.

PCR primer pairs can be derived from a known sequence, for example, by using computer programs intended for that purpose. One of ordinary skill in the art will appreciate that the specificity of a particular probe or primer increases with its length. Thus, in order to obtain greater specificity, probes and primers can be selected that comprise at least 17, 20, 23, 25, 30, 35, 40, 45, 50 or more consecutive nucleotides of the target sequence being amplified.

Quantitative real time PCR: A method for detecting and measuring products generated during each cycle of a PCR, which products are proportionate to the amount of template nucleic acid present prior to the start of PCR. The information obtained, such as an amplification curve, can be used to quantitate the initial amounts of template nucleic acid sequence.

Reverse transcription: Production of DNA from an RNA template, by the enzyme reverse transcriptase. The DNA product of a reverse transcription reaction is known as cDNA.

Sequence identity: The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are. Methods of alignment of sequences for comparison are well known in the art.

An alternative indication that two nucleic acid molecules are closely related is that the two molecules hybridize to each other under stringent conditions. Stringent conditions are sequence-dependent and are different under different environmental parameters. Generally, stringent conditions are selected to be about 5° C. to 20° C. lower than the thermal melting point $(T_m)$ for the specific sequence at a defined ionic strength and pH. The $T_m$ is the temperature (under defined ionic strength and pH) at which 50% of the target sequence remains hybridized to a perfectly matched probe or complementary strand. Conditions for nucleic acid hybridization and calculation of stringencies can be found in Sambrook et al. (ed.), *Molecular Cloning: A Laboratory Manual,* $2^{nd}$ ed., vol. 1-3, Cold Spring Harbor Laboratory Press, Cold Spring Harbor, N.Y., 1989, and Tijssen *Laboratory Techniques in Biochemistry and Molecular Biology— Hybridization with Nucleic Acid Probes* Part I, Chapter 2, Elsevier, New York, 1993.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the Na+ concentration) of the hybridization buffer will determine the stringency of hybridization, though waste times also influence stringency. Calculations regarding hybridization conditions required for attaining particular degrees of stringency are standard. The following is an exemplary set of hybridization conditions:

Very High Stringency (Detects Sequences that Share 90% Identity)
    Hybridization: 5×SSC at 65° C. for 16 hours
    Wash twice: 2×SSC at room temperature (RT) for 15 minutes each
    Wash twice: 0.5×SSC at 65° C. for 20 minutes each
High Stringency (Detects Sequences that Share 80% Identity or Greater)
    Hybridization: 5×-6×SSC at 65° C.-70° C. for 16-20 hours
    Wash twice: 2×SSC at RT for 5-20 minutes each
    Wash twice: 1×SSC at 55° C.-70° C. for 30 minutes each
Low Stringency (Detects Sequences that Share Greater than 50% Identity)
    Hybridization: 6×SSC at RT to 55° C. for 16-20 hours
    Wash at least twice: 2×-3×SSC at RT to 55° C. for 20-30 minutes each.

System of Treatment: A multi-step health care method directed by a single actor (through their employees or contracted agents), such as a public health care provider (e.g. a national health service or provider thereof), health maintenance organization (HMO), or hospital organization. While individual steps with a system of treatment can be carried out by multiple actors, the total method is organized by a single actor from whom the health care is provided.

III. Overview of Several Embodiments

Provided herein are method of prognosis of acute lymphoblastic leukemia (ALL) in a subject, by determining the expression level of miR-1290 in a sample from the subject (such as a bone marrow sample); and comparing the miR-1290 expression level in the subject with control expression of miR-1290, wherein a significant increase in miR-1290 expression in the subject in comparison to the control expression indicates that the subject has an increased risk of ALL relapse; and wherein a significant decrease in miR-1290 expression in the subject in comparison to the control expression indicates that the subject has a reduced risk of ALL relapse.

Also provided are methods of prognosis of acute lymphoblastic leukemia (ALL) in a subject, by determining the expression level of miR-1290, and at least one of miR-151-5p and miR-451 in a sample from the subject (such as a bone marrow sample); and comparing the determined expression of miR-1290, and miR-151-5p and/or miR-451 with control expression of miR-1290, and miR-151-5p and/or miR-451, wherein a significant increase in miR-1290 expression in the subject in comparison to the control miR-1290 expression, combined with a significant decrease in expression of the at least one of miR-151-5p and miR-451 in comparison to the control expression of miR-151-5p and/or miR-451, indicates that the subject has an increased risk of ALL relapse; and wherein a significant decrease in miR-1290 expression in the subject in comparison to the control expression, combined with a significant increase in expression of the at least one of miR-151-5p and miR-451 in comparison to the control expression of miR-151-5p and/or miR-451, indicates that the subject has a reduced risk of ALL relapse.

In particular embodiments, the control level of miR-1290, miR-151-5p, and miR-451 are separate cutoff values.

In other particular embodiments, the risk of ALL relapse in the subject is further correlated with ALL-associated clinical criteria selected from the group consisting of: B-ALL and T-ALL diagnosis, minimal residual disease (MRD) high and low risk definitions, response to prednisone on day 8 of treatment; BFM high, intermediate, and low risk definitions, white blood count (WBC) being over or below 20,000 cells/ml, patient age being over one and under six years old or otherwise, CCG high and low risk definitions, and gender.

In particular embodiments, the subject has been diagnosed with B-ALL.

In further embodiments, the determination that a subject has an increased risk of ALL relapse predicts that the subject could benefit from a treatment comprising at least of a NAMPT or JAK2 inhibitor.

Further described herein are systems of ALL treatment that include determining the expression level of miR-1290 in a sample from the subject (such as a bone marrow sample or a blood sample); comparing the miR-1290 expression level in the subject with control expression of miR-1290, wherein a significant increase in miR-1290 expression in the subject in comparison to the control expression indicates that the subject has an increased risk of ALL relapse, and requires treatment appropriate for a subject with an increased risk of ALL relapse; and administering to the patient an ALL treatment designated as appropriate for a patient with an increased risk of ALL relapse.

An additionally described system of ALL treatment includes determining the expression level of miR-1290 and at least one of miR-151-5p and miR-451 in a sample from a subject (such as a bone marrow sample); and comparing the determined expression of miR-1290, and miR-151-5p and/or miR-451 with control expression of miR-1290, and miR-151-5p and/or miR-451, wherein a significant increase in miR-1290 expression in the subject in comparison to the control miR-1290 expression, combined with a significant decrease in expression of the at least one of miR-151-5p and miR-451 in comparison to the control expression of miR-151-5p and/or miR-451, indicates that the subject has an increased risk of ALL relapse, and requires treatment appropriate for a subject with an increased risk of ALL relapse; and administering to the patient an ALL treatment designated as appropriate for a patient with an increased risk of ALL relapse.

In particular embodiments of the described systems, the control expression of miR-1290, miR-151-5p, and miR-451 are separate cutoff values.

In particular embodiments of the systems, the risk of ALL relapse in the subject is further correlated with ALL-associated clinical criteria selected from the group consisting of: B-ALL and T-ALL diagnosis, minimal residual disease (MRD) high and low risk definitions, response to prednisone on day 8 of treatment; BFM high and low risk definitions, white blood count (WBC) being over or below 20,000 cells/ml, patient age being over one and under six years old or otherwise, CCG high and low risk definitions, and gender.

In still further embodiments of the systems, the subject has been diagnosed with B-ALL.

In particular embodiments, the subject has an standard (pre-induction therapy non-high) risk of relapse or a high risk of relapse.

In other particular embodiments the treatment is a protocol for patients determined to have a high risk of ALL relapse, such as a treatment that includes a composition comprising an anthracycline.

IV. ALL Prognosis by Detection of miR-1290, miR-151-5p, and miR-451

Prediction of relapse has proved to be the key for successful treatment of pediatric ALL. Described herein is the observation that even on the day of ALL diagnosis, differences in miRNA expression are predictive of disease relapse, and indicative of the appropriate form of treatment recommended for the patient. In particular, described herein is the observation that overexpression of miR-1290 correlates with ALL relapse, and the predictive power of combination determinations of miR-151 and miR-451 expression (underexpressed, compared with a standard), and miR-1290 expression (overexpressed, compared with a standard) is greater than any subcombination thereof. An increased risk of ALL relapse is accordingly predictive that the patient would benefit from an ALL high risk treatment, as described herein.

Current practice for ALL treatment includes determining the risk of disease relapse following standard treatment. The determined risk prognosis is determinative of the treatments given to the patient. Standard prognosis determining methods include the COG, BFM, MRD, UKALL, CCLG, DFCI systems, from which a patient is determined to be high risk (HR), intermediate risk (IR), and standard risk (SR). Accordingly, under current practice, ALL treatment is provided as a risk-based treatment, i.e., high risk patients receive a more intensive treatment while the standard risk patients receive treatment reduction.

According to the BFM system (Vrooman L M et al., Curr Opin Pediatr. (2009); 21:1-8), standard risk includes (1) no adverse cytogenetics, (2) age between 1 and 6 years, (3) good response to prednisone treatment on day 8. High risk includes at least one of (1) cytogenetic abnormalities (e.g. t(9;22) and t(4;11)), (2) under 1 year of age or above 6 years, (3) poor response to prednisone treatment on day 8 and (4) hypodiploidy. Intermediate risk includes those whose age is between 1 to 6, show no adverse cytogenetics, no hypodiploidy and a good response to prednisone on day 8 of treatment, as well as those whose condition does not meet the criteria for either standard risk or high risk.

An alternative definition of relapse risk is MRD diagnosis, which is based on an indication of the amount of remaining leukemic blasts in a patient's bone marrow (BM) during and/or after treatment, which can be measured by means of flow cytometry. (FACS) and polymerase-chain reaction (PCR) (van Dongen J J M et al., Lancet. (1998); 352:1731-1738). MRD risk stratification is performed after MRD analysis on days 33 and 78 from the beginning of treatment. MRD standard risk is defined as a negative MRD finding on day 33 and on day 78. MRD high risk is defined as a finding of 10-3 leukemic cells (1 leukemic cell in 1000 normal cells) on day 78. All other findings are defined as intermediate risk. In the present invention, the MRD test was performed by PCR amplification of immunoglobulin and T-cell rearrangement sites (PCR-MRD), and interpreted according to the guidelines of the European Study Group for MRD detection in ALL (ESG-MRD-ALL).

Patients receive the same treatment until risk stratification is defined following the results obtained from MRD analysis after day 78 of treatment.

According to the COG system (Smith et al., *J Clin Oncol.* (1996); 14:18-24; Hunger, *Am Soc Clin Oncol Educ Book* (2012); 611-615), NCI standard risk includes (1) WBC count less than 50,000/μL and (2) age 1 to younger than 10 years. NCI high risk includes (1) WBC count 50,000/μL or greater and/or (2) age 10 years or older.

In typical therapies according to the COG protocol, Induction drugs are given at first four weeks of treatment. NCI standard risk without CNS3 or overt testicular disease induction drugs includes, among other treatments: (1) dexamethasone, (2) vincristine and (3) asparaginase. NCI high risk drugs or with CNS3 or overt testicular disease includes (1) dexamethasone, (2) vincristine, (3) asparaginase and (4) an anthracycline such as daunorubicin. Following the initial phase of treatment, other differences in provided therapeutics between high and non-high risk relapse patients includes administration of cyclophosphamide, continued vincristine, and asparaginase. Other differences between high and non-high risk COG (as well as BFM) treatments are known to the art (Borowitz et al., Blood (2008); 111:5477-5485; and summarized in Hunger, *Am Soc Clin Oncol Educ Book.* 2012, 611-615). In the COG protocol MRD is measured in blood at day 8 and bone marrow at day 29 and is used together with other prognostic factors to determine at post-induction if the patient risk for relapse is low/average/high/very high and the method of post-induction treatment.

The described methods therefore not only allow for improved determination of ALL prognosis and relapse risk, but also improved overall systems of treatment for ALL, which include providing the most appropriate treatment protocol as determined by the determined relapse risk at a significantly earlier time point than currently achievable with MRD testing. In particular, the described methods allow for a health care provider to determine whether a subject, such as a subject determined to have an increased chance ALL relapse (using the described methods), would benefit from a "high risk" treatment protocol known to the art, such as, but not limited to, the HR BFM or HR COG treatment protocols. Further, as described herein, NAMPT and JAK2-induced phosphorylated proteins are upregulated in cells that underexpress miR-451 and overexpress miR-1290, respectively. Therefore, the described methods also allow a health care provider to predict whether a patient could benefit from treatments involving provision of NAMPT and/or JAK2 inhibitors.

Accordingly, provided herein are methods for the prognosis of ALL in a subject, by determining the level of expression of miR-1290, alone or in combination with the expression of miR-151-5p and/or miR-451, and comparing the determined expression to a control or standard, such as a predetermined cutoff value. In a particular embodiment, the expression of miR-1290 is detected. In another embodiment, the expression of miR-1290 and miR-151-5p is detected. In yet another embodiment, the expression of miR-1290 and miR-451.

In the described methods, the expression in the subject sample of miR-1290, alone or in combination with the expression of miR-151-5p and/or miR-451 is compared to the expression of the specific miRNAs in a control sample, wherein a comparative significant increase in miR-1290 expression alone or in combination with a significant decrease in at least one of miR-151-5p and miR-451 indicates an increased risk of ALL relapse. An increased risk of ALL relapse as determined by the methods described herein, indicates that the subject would benefit from a treatment protocol currently administered to subjects grouped as "high risk" for ALL relapse. As understood herein, a control is a standard defined by the amount of specific miRNA expression in samples from one of more subjects who are either ALL free, or alternatively who had ALL but did not relapse. Such standards can change over time as additional patient data is accumulated.

In some embodiments, the predetermined control value to which a subject sample is compared, is described as a cutoff value, wherein a departure from the cutoff indicates a significant difference from the control value, and an increased risk of ALL relapse. In such embodiments, the expression of the miRNAs in relation to the cutoff value determines how the patient should be grouped with those pre-established ALL patient populations associated with specific relapse rates. For example, determination that a patient is expressing miR-1290 at levels greater than a cutoff, combined with determination that at least one of miR-151-5p and miR-451 are expressed lower than a cutoff indicates that the patient has higher risk for relapse than a patient that does not exhibit such miRNA expression levels. As used herein, such expression (a detected downregulation of miR-151-5p and miR-451, and a detected upregulation of miR-1290) can be termed a "positive expression value"

As described herein, a "cutoff value", sometimes referred to as a "cutoff", is a value that meets the requirements for both high diagnostic sensitivity (true positive rate) and high diagnostic specificity (true negative rate). Determined cutoff values are the result of a statistical analysis of miRNA expression value differences in pre-established populations which either relapsed or remained disease-free.

It should be emphasized that the accumulation of further patient data may improve the accuracy of the presently provided cutoff values, which in particular embodiments can be based on an ROC (Receiver Operating Characteristic) curve generated according to said patient data using, for example, a commercially available analytical software program. The miR-151-5p and/or miR-451 expression values are selected along the ROC curve for optimal combination of prognostic sensitivity and prognostic specificity which are as close to 100% as possible, and the resulting values are used as the cutoff values that distinguish between patients who will relapse at a certain rate, and those who will not (with said given sensitivity and specificity). The ROC curve may evolve as more and more patient-relapse data and related miR-151-5p, miR-451, and miR-1290 expression values are recorded and taken into consideration, modifying the optimal cutoff values and improving sensitivity and specificity. Thus, the provided cutoff values for miR-151-5p and miR-451 should be viewed as not limiting, but merely illustrative of the statistical analysis.

In a particular embodiment, the cutoff values for miR-151-5p and miR-451 respectively are 0.00015 and 0.001 (units relative to expression of an internal standard; the determination of which is described in International Patent Application No. PCT/IL2011/000754). Accordingly respective miR-151-5p and miR-451 expression levels that are lower than 0.00015 and 0.001 indicates that a subject is expressing these miRNAs at significantly lower levels than a control. With regard to miR-1290, if a subject is determined to be expressing miR-1290 above a determined cut-off value, the subject is identified as expressing miR-1290 at significantly higher levels than a control.

In particular embodiments, the determination of the miR-1290 expression combined with determination at least one of miR-151-5p and miR-451 is correlated with particular risks of relapse, depending on the determined expression levels. In other embodiments, the determined miRNA expression is combined with other clinical features, including white blood cell (WBC) count, age, minimal residual disease (MRD) risk index, cytogenetic aberrations, response to prednisone treatment on day 8, and ploidy to determine disease prognosis and relapse risk.

In particular embodiments, the ALL patient population group that may be examined by the described methods is optionally further defined by sub-grouping of the patient according to at least one clinical criterion, and each patient sub-group belongs to a specific pre-established ALL patient population associated with a specific relapse rate. According to certain embodiments, the clinical criteria comprise sub-groupings according to: B-ALL and/or T-ALL diagnosis; minimal residual disease (MRD) high, intermediate, and low risk definitions; response to prednisone on day 8 of treatment; BFM high and low risk definitions; white blood count (WBC) being over or below 20,000 cells/ml; patient age being over one and under six years old or otherwise; CCG high and low risk definitions; and gender.

Typically, a good response to prednisone on day 8 of treatment is defined as a finding of less than 1000 leukemic blast cells/ml of blood, whereas a poor response is defined as a finding of more than 1000 leukemic blast cells/ml of blood.

In particular embodiments, the method of the invention is specifically applicable for predicting B-ALL relapse.

The miRNAs described herein can be detected by any methods known to the art, including use of standard oligonucleotides primers and probes, each of which can specifically hybridize to a nucleic acid sequence of at least one of miR-151-5p (SEQ ID NO: 1), miR-451 (SEQ ID NO: 2), and miR-1290 (SEQ ID NO: 3), and of at least one control reference miRNA. Such sequences include sequences that are 100% identical to the reverse complement of SEQ ID NOs 1-3. It is understood that such primers and probes can also be less than identical to the reverse complement of SEQ ID NOs 1-3, such as 98%, 95%, 90%, 85% or even less, and that the design of such primers is well known in the art.

It will be appreciated however, that although certain techniques can utilize standard primers and probes, the miRNA 18-24 nt length precludes use of simple amplification techniques. In particular embodiments, miRNA is detected using a DNA microarray, wherein miRNA is extracted from a sample, reverse transcribed, labeled and exposed to DNA microarray with match oligos. miRNA amounts are quantified by measured fluoresence after washing non specifically bound reverse transcribed sequences.

In another embodiment, miRNA can be measured by adding a poly-A tract to extracted RNA, reverse transcribing the poly-adenylated RNAs using a poly-A primer, followed by miRNA-sequence specific qPCR, with specific (miRNA-specific) and non-specific (poly-AA) primers.

Figure 12:
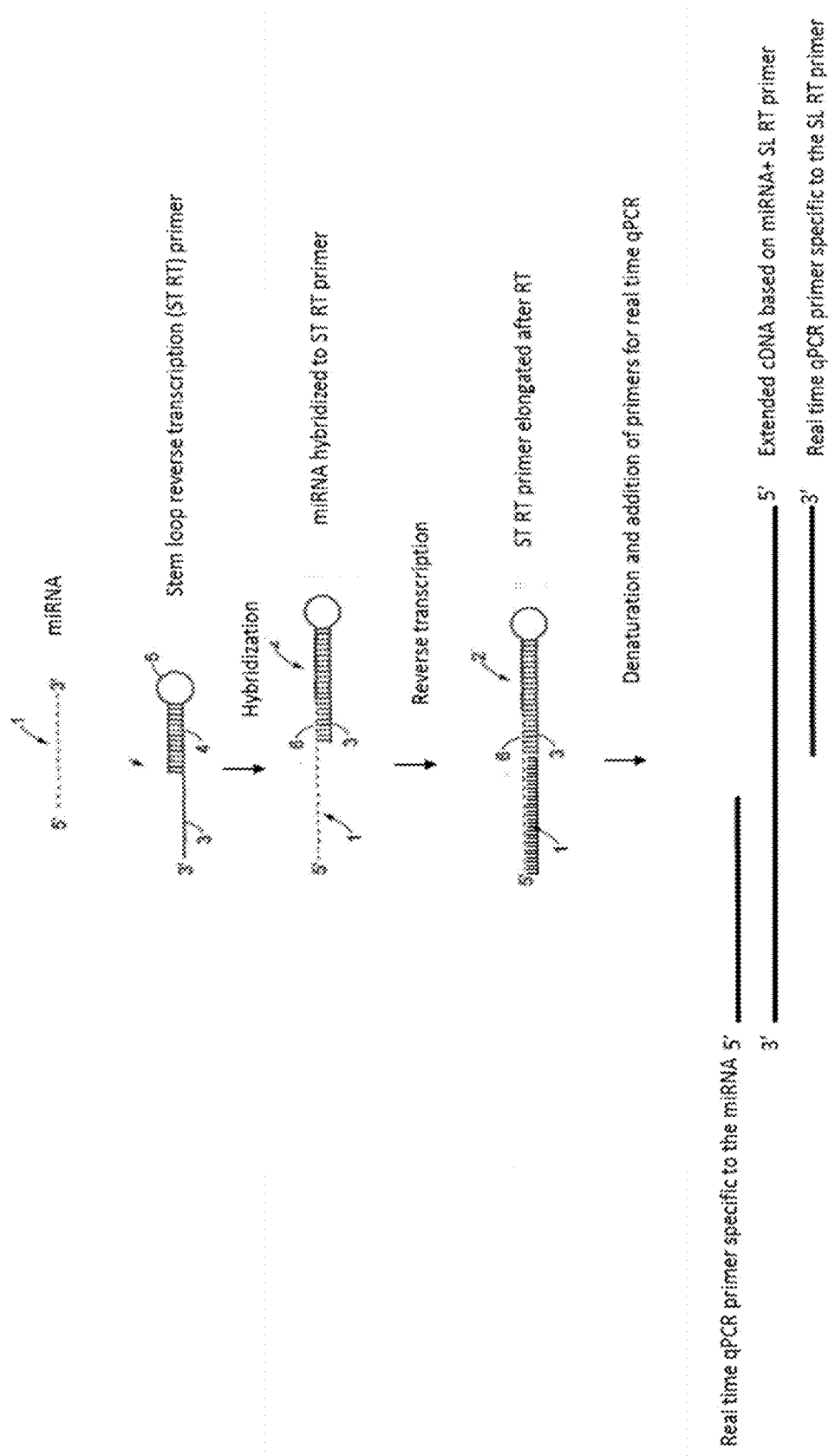
FIG. 12 is a schematic overview of miRNA amplification by RT-qPCR, using a stem-loop oligonucleotide primer.

In yet another embodiment, extracted miRNA is reverse transcribed using an miRNA structure-specific stem-loop primer. The reverse transcribed miRNA sequences are then amplified and quantified by qPCR with miRNA sequence-specific forward primers and a backward primer specific to the miRNA loop. Design of miRNA stem-loop primers and their use in RT-qPCR is described in Kramer, *Curr. Prot in Molec. Biol.* 15:10, July 2011 (available online at ncbi.nlm.nih.gov/pmc/articles/PMC3152947/). Non-limiting examples of stem-loop primers for use in reverse transcribing miR-151-5p, miR-451, and miR-1290 are based on the description in Kramer (*Curr. Prot in Molec. Biol.* 15:10, July 2011), and are set forth as SEQ ID NOs 6-8, respectively. Use of a stem-loop primer in RT-qPCR is illustrated in FIG. 12 (see also Chen et al. *NAR*, 33:e179, 2005).

Non-limiting examples of standard nucleic acid detection methods include PCR (in all of its forms, including qPCR), nucleic acid microarrays, Northern blot analysis, and various forms of primer extension.

Primers and probes for use in detecting the described miRNAs can be RNA or DNA, or analogs thereof. Examples of DNA/RNA analogs include, but are not limited to, 2-'O-alkyl sugar modifications, methylphosphonate, phosphorothiate, phosphorodithioate, formacetal, 3-thioformacetal, sulfone, sulfamate, and nitroxide backbone modifications, and analogs, for example, LNA analogs, wherein the base moieties have been modified. In addition, analogs of oligomers may be polymers in which the sugar moiety has been modified or replaced by another suitable moiety, resulting in polymers which include, but are not limited to, morpholino analogs and peptide nucleic acid (PNA) analogs. Probes may also be mixtures of any of the oligonucleotide analog types together or in combination with native DNA or RNA. In particular embodiments, the oligonucleotides and analogs can be used alone; in other embodiments, they can be used in combination with one or more additional oligonucleotides or analogs.

In a particular embodiment, the described oligonucleotides are any one of a pair of primers or nucleotide probe, for use in detecting the level of expression of miR-1290 and at least one of miR-151-5p and miR-451, using a nucleic acid amplification assay including but not limited to Real-Time PCR, micro arrays, PCR, in situ Hybridization and Comparative Genomic Hybridization. Methods and hybridization assays using self-quenching fluorescence probes with and/or without internal controls for detection of nucleic acid application products are known in the art, for example, U.S. Pat. Nos. 6,258,569; 6,030,787; 5,952,202; 5,876,930; 5,866,336; 5,736,333; 5,723,591; 5,691,146; and 5,538,848.

In particular embodiments, in addition to detection of the miR of interest (miR-1290, etc.), the particular detection methods also utilizes primers and/or probes to detect the expression of a nucleic acid to be used as an internal normalizing control. According to this embodiment, the detecting nucleic acid molecules used by the described methods include isolated oligonucleotides that specifically hybridize to a nucleic acid sequence of miR-1290 and at least one of miR-151-5p and miR-451; and isolated oligonucleotides that specifically hybridize to a nucleic acid sequence of at least one reference RNA. Non-limiting examples of such reference RNAs include a reference miRNA (whose expression is known to be the same, regardless of ALL condition), the 5S ribosomal RNA (rRNA), the U6 small nuclear RNA, or the miRXplore Universal Reference (UR) (Miltenyi biotech), which represents a pool of 979 synthetic miRNA for comparison of multiple samples.

The described methods relate to prognosis of ALL based on examining the expression of certain miRNA's, specifically, miR-151-5p, miR-451, and miR-1290 in a test sample, specifically, a biological sample obtained from a subject, methods of processing such samples to isolate nucleic acids for use in the described methods are known to the art. In particular embodiments, the sample is derived from the bone marrow of the subject. In other particular embodiments, the sample is a blood sample.

The described methods are directed to determining the expression levels of miR-151-5p, miR-451, and miR-1290. As described herein, the observation in a patient that miR-151-5p and miR-451 are underexpressed (relative to a control) and that mir-1290 is overexpressed (relative to a control) is indicative of an increased risk of relapse. Accordingly, such patients could benefit from more intensive ALL therapy. However the converse situation is also true: in particular embodiments, detection of miRs in a sample, as described herein, and the observation that miR-151-5p and miR-451 are overexpressed (relative to a control) and that mir-1290 is underexpressed (relative to a control) is indicative of a reduced risk of relapse, and even a greater responsiveness to standard treatment. Such observations are predictive that such patients could benefit from a reduction in the intensity of the ALL therapy (see for example Conter et al., Blood 115:3206-3214, 2010).

In particular embodiments, the methods described herein are employed at a single time point after a subject (patient) is diagnosed. In other embodiments, the methods described herein can be used to monitor the progress of a patient and whether their prognosis for relapse changes over time. Multiple time points can be used in such monitoring, for example, 1, 2, 3, 4, 5, or 6 months or more after diagnosis and treatment initiation (and any time point in between) can be suitable timepoints to measure the expression of miR-151-5p, miR-451, and mir-1290 in a sample from the patient.

Also described herein are the observations that underexpression of miR-451 leads to an increase in NAMPT, and overexpression of miR-1290 leads to increase of JAK2. Both NAMPT and JAK2 overexpression have been associated with various cancers. Accordingly, the described methods of determining abnormal expression of miR-451 and/or miR-1290 in a subject also allows prediction that the subject would benefit from a treatment employing a NAMPT and/or JAK2 inhibitor, as appropriate.

V. Systems of ALL Treatment

Additionally described herein are systems of treating an ALL patient. The described systems involve first determining the risk of ALL relapse, through the described methods of detecting the expression of miR-1290, and at least one of miR-151-5p and miR-451. Once it is determined that a subject has an increased risk of ALL relapse, an appropriate treatment is given, tailored to the determined relapse risk.

As described herein, typical treatments for ALL patients are determined by the prognosis of a high or non-high risk of relapse. Standard protocols (for example, but not limited to, BFM high risk and COG high risk, see Borowitz et al., Blood (2008); 111:5477-5485; and summarized in Hunger, *Am Soc Clin Oncol Educ Book.* 2012, 611-615), have been developed to treat high risk patients more intensively than non-high risk patients and reduce treatment intensity in standard risk patients. Among the differences in such drug protocols between patients who have a high and non-high risk of relapse includes early use of an anthracylcine drug such as daunorubicin in the course of treatment.

Prior to the described systems, determining appropriate ALL treatment not only relied on entirely different clinical parameters (e.g. WBC count, prednisone response), but such determinations were made days or even weeks after the initial diagnosis. In contrast, the current systems can determine appropriate treatment at the time of initial ALL diagnosis, following a test for expression of miR-1290, and at least one of miR-151-5p and miR-451. Once a determination is made that a patient may have an increased risk of relapse, a "high risk" treatment protocol (such as those employing an anthracycline) can be administered.

The current systems are based on the understanding that modern healthcare services are provided by large entities within which multiple healthcare services are given to a patient. Particular non-limiting examples of such entities include physicians groups, hospital consortiums or networks, and public or private health maintenance organizations. Within these entities, a patient's health care may be managed by a single actor, such as a physician, nurse practitioner, and the like, but specialized services are provided to the patient by multiple actors within the system, such as diagnosticians and specialists. It is recognized that in particular embodiments, certain services may be outsourced to a provider outside of the main service provider. Therefore, the diagnostician may be different from the primary physician or oncologist. However, in all embodiments, it is the main service provider, or representative or employee thereof, who is directing the described systems of treatment.

The following examples are provided to illustrate certain particular features and/or embodiments. These examples should not be construed to limit the disclosure to the particular features or embodiments described.

EXAMPLES

Example 1: General Methods

Patient Material Collection:

Bone marrow (BM) biopsies at the time of diagnosis were obtained from 95 pediatric ALL patients and the percentage of leukemic blasts in those samples was at least 80%. 53 males and 42 females, median age 6.6 years (range 0.3-18), 28 patients had T-ALL, 46 patients had a WBC>20000, 18 patients were poor prednisone responders, 32 patients were clinically classified as BFM high-risk, 40 intermediate-risk and 23 standard-risk, 31 patients relapsed. The median follow-up of patients was 69 months (range 6-296). All patients were treated at Schneider children's medical center of Israel. 4, 16, 25 and 50 patients were treated according to the INS-84, INS-89, INS-98 and INS-2003 protocols respectively (all of which are part of the general BFM study and protocol) [Stark B et al., Leukemia. (2010); 24: 419-424; INS-2003].

RNA Isolation:

RNA was isolated out of $10^7$ cells from BM biopsies according to the miRNeasy mini kit (Qiagen). RNA concentration was determined by measuring the absorbance at 260 nm with a $A_{260}/A_{280}$ ratio of 1.8.

miRNA Expression Profile:

Microarray analysis was performed on 48 ALL samples using the Miltenyi biotech microarray platform (Miltenyi biotech, Germany) RNA quality was assessed by Agilent 2100 Bioanalyzer platform (Agilent technologies) and visualized by means of agarose gel electrophoresis. Sample labeling was performed according to the miRXplore™ microarray platform user manual (Miltenyi biotech, Germany). For those samples which revealed a sufficient RNA yield, 2 µg total RNA were used for the labeling, for all other samples the available amount of total RNA was used. Subsequently, the fluorescently labeled samples were hybridized overnight to miRXplore™ microarrays using the a-Hyb™ hybridization station (Miltenyi biotech, Germany) Control samples were labeled with Hy3 and experimental samples were labeled with Hy5. The miRXplore Universal Reference (UR) was used as control samples and it represents a pool of 979 synthetic miRNA for comparison of multiple samples. Fluorescent signals of the hybridized miRXplore™ microarray were detected using a laser scanner from Agilent (Agilent technologies). Normalized Hy5/Hy3 ratios were calculated for each quadruplicate by PIQOR™ analyzer (Miltenyi biotech, Germany). Only miRNAs that had a signal that was equal or higher than the 50% percentile of the background signal intensities were used for the Hy5/Hy3 ratio calculation. Data was transformed to Log 2 ratios for data clustering (2D-clustering using Pearson correlation and average linkage).

qRT-PCR:

miRNA-microarray results were verified by qRT-PCR on 95 samples. cDNA was made from 100 ng according to the manufacturer instructions (Exiqon, Denmark). qRT-PCR was performed with LNA™ primers (Exiqon) for the selected miRNAs. The 5S rRNA was used as a reference. qRT-PCR was performed in duplicate with the LightCycler 480.

Statistical Analyses:

miRNA expression data were analyzed with PASW Statistics 18 (SPSS Inc. Chicago, Ill.). For correlation with age, gender, WBC, d8, type and risk group the Fisher's exact test was used. In order to determine the optimal cutoff value, ROC analysis was performed for each miRNA. Kaplan-Meier analyses were performed to evaluate whether the selected miRNA correlate with relapse and COX-regression was used to determine whether those miRNA can be regarded as independent risk factors. A p-value of <0.05 was considered as significant for the survival analyses.

Example 2: miR-151-5p, miR-451 and miR-1290 Expression Correlates with Various ALL Clinical Parameters This example shows that ALL prognosis can be accurately predicted by decreased expression of the miR-151-5p and miR-451, accompanied by an increased expression of miR-1290.

Microarray analysis was used to determine ALL-specific miRNA expression. From a panel of 979 synthetic miRNA, only 116 were significantly higher and 116 were significantly lower, relative to the universal reference (UR). Clustering with age, type, WBC, d8, risk group and relapse revealed 10, 33, 20, 14, 19 and 33, respectively, miRNA that were significantly lower expressed in ALL, while 9, 36, 16, 12, 14 and 28 (respectively) miRNA were significantly higher expressed in ALL. Analysis of the lower-expressed miRNAs was described in International Patent Application No. PCT/IL2011/000754, the entirety of which is incorporated by reference herein. Therein, it was described that combined decrease in miR-151-5p and miR-451 expression is predictive of increased risk of ALL relapse and worse disease prognosis.

In a further analysis of the miR-ALL microarray, 4 miRs were chosen that were upregulated and associated with at least 3 adverse prognostic markers: miR-196b, miR-424, miR-1248, and miR-1290. To confirm the correlation between expression and ALL, the expression levels of these 4 miRs were further analyzed by real-time quantitative PCR in a cohort of 125 pediatric ALL patients (B-lineage and T-cell). Of the 4 miRs analyzed, only miR-1290 significantly correlated with ALL outcome.

Figure 2:
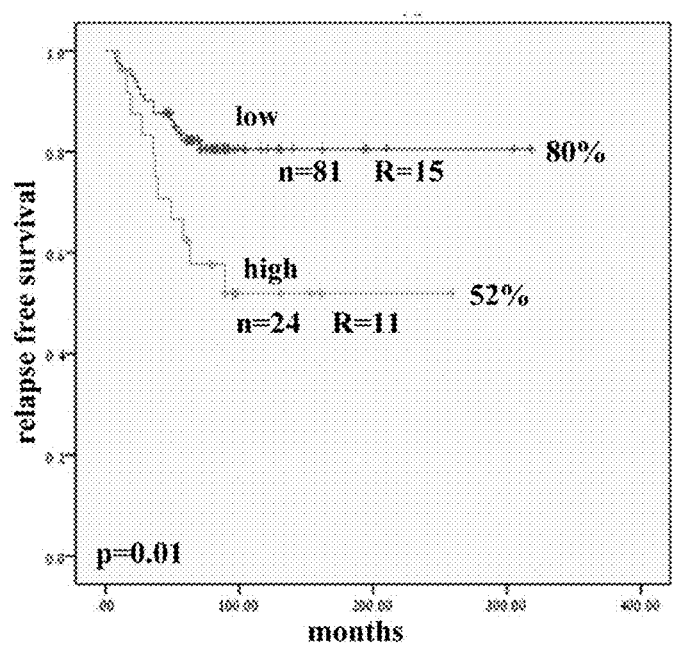
FIG. 2 is a Kaplan Meier plot of relapse free survival only for B-lineage ALL cohort (n=105). In the plot, the line representing high or low expression of miR-1290 is accordingly indicated.

Using quartile 3 as a cut-off, patients expressing high levels of miR-1290 had a 48% relapse free survival (RFS) versus 77% RFS in those expressing low levels of the miR (p=0.005, FIG. 1). When the median expression level was used as the cut-off, the significant correlation with outcome was maintained. RFS was 59% for those expressing high levels versus 81% for those expressing low levels of the miR (p=0.017, data not shown). A significant correlation with outcome was also observed when analyzing only the B-lineage ALL patients (n=105). Patients expressing high levels of miR-1290 had a 52% RFS versus 80% for those expressing low levels (p=0.010; FIG. 2).

When applying multivariate cox regression analysis with the variants: miR-1290, age, WBC, and prednisone response in the B-lineage cohort, both miR-1290 and WBC were identified as significant independent prognostic markers. From this analysis, it was determined that a patient expressing high levels of miR-1290 has a 3 fold increased risk of relapse (Table I).

TABLE A

Multivariate cox regression analysis for relapse in the B-lineage cohort (n = 105)

| Variant | Univariate p | Multivariate | | |
|---|---|---|---|---|
| | | p | HR | 95% CI |
| miR-1290 high vs low expression | 0.010 | 0.006 | 3.03 | 1.4-6.6 |
| Age 1 to 6 vs <1 or >6 years | NS | | | |
| WBC below versus above 20 × 109/L | 0.001 | 0.001 | 3.8 | 1.7-8.4 |
| Prednisone response poor versus good | NS | | | |

Currently, the risk of ALL relapse is based on the detection of minimal residual disease following treatment on days 33 and 78 from diagnosis. The amount of residual leukemic cells determines the risk groups and treatment is adjusted accordingly. The aim is to increase treatment in the high risk group, and reduce in the favorable group. Multivariate cox regression analysis was applied again including the MRD data, which was available for 61 B-lineage ALL patients. All patients excluding 2, were MRD non-high risk patients. A patient expressing high levels of miR-1290 had an increased risk fold of 4.8 to relapse (p=0.027; Table II).

TABLE B

Multivariate cox regression analysis for relapse in the B-lineage MRD non-high risk cohort (n = 61)

| Variant | Univariate p | Multivariate | | |
|---|---|---|---|---|
| | | p | HR | 95% CI |
| miR-1290 high vs low expression | 0.014 | 0.027 | 4.8 | 1.2-19.5 |
| Age 1 to 6 vs <1 or >6 years | NS | | | |
| WBC below versus above 20 × 109/L | 0.037 | 0.055 | 4.1 | 0.1-17.2 |
| Prednisone response poor versus good | NS | | | |
| MRD | NS | | | |

Figure 3:
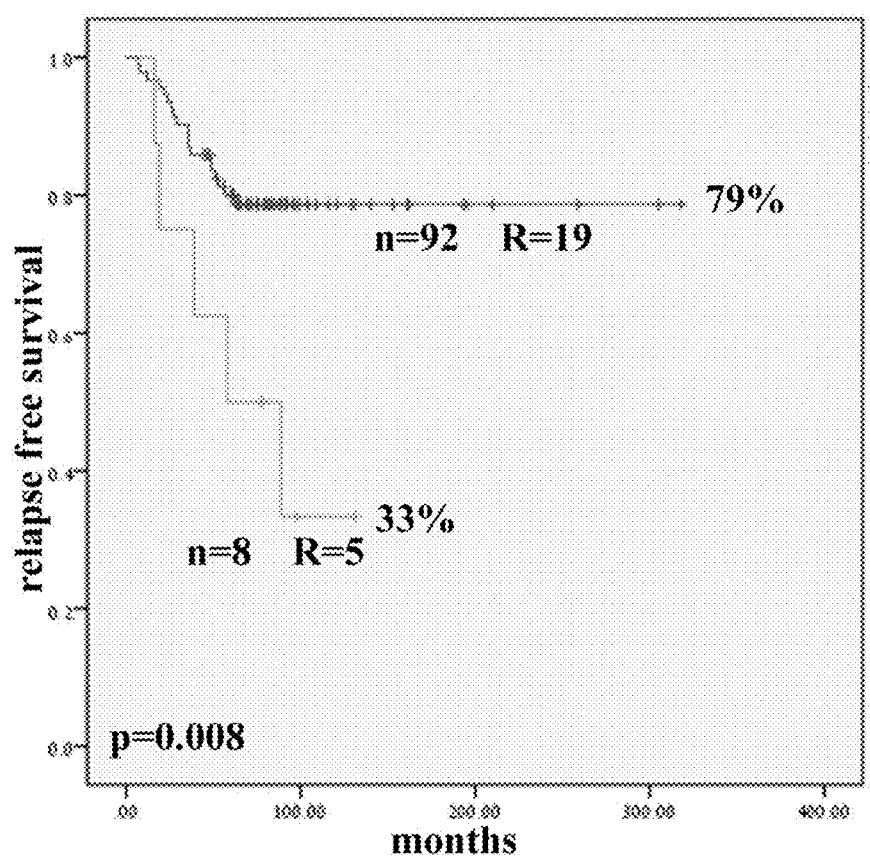
FIG. 3 is a Kaplan Meier analysis for relapse-free survival by expression levels of the combined miRs: both downregulated miRs together with the upregulated miR-1290 in precursor B-cell ALL patients. The lower line represents a combination of down-regulated miR-451 and miR-151-5p, and up-regulated miR-1290. The upper line represents all other expression combinations for miR-451, miR-151-5p, and miR-1290.

When data related to the downregulated and upregulated miRs was combined, it was revealed that the patients expressing low levels of both miRs together (miR-151 and miR-451) with high levels of miR-1290 had a very poor outcome; 33% versus 79% RFS for all other combinations (p=0.008; FIG. 3).

When Multivariate Cox regression analysis was applied to the risk of relapse in the combined results of the down and up-regulated miRs, it was shown that a patient expressing low levels of both miR-151 and miR-451) with high levels of miR-1290, had an increased risk of 16.7 to relapse (p=0.006; Table III).

TABLE C

Multivariate Cox regression analysis for relapse in the PCR-MRD non-high risk cohort (n = 54)

| Variant | Univariate p | Multivariate | | |
|---|---|---|---|---|
| | | p | HR | 95% CI |
| Combination of all 3 miRs | 0.02 | 0.006 | 16.7 | 2.3-122 |
| Upregulated miR-1290 | 0.021 | | | |
| Both miR-151 and miR-451 downregulated | 0.06 | | | |
| Age 1 to 6 vs <1 or >6 years | NS | | | |
| WBC below versus above 20 × 10$^9$/L | 0.037 | | | |
| Prednisone response poor versus good | NS | | | |
| MRD | 0.075 | 0.017 | 6.9 | 1.4-33 |

Based on these analysis it can be concluded that combining detection of miR-151, miR-451, and miR-1290 together, very high risk patients can be accurately detected, within a cohort of non-high risk patients, so that those patients at high risk of relapse could benefit from a more intensive therapy, already at the time of diagnosis.

Example 3: Up-Regulation of miR-451 Decreases ALL Cell Growth

Figure 4A:
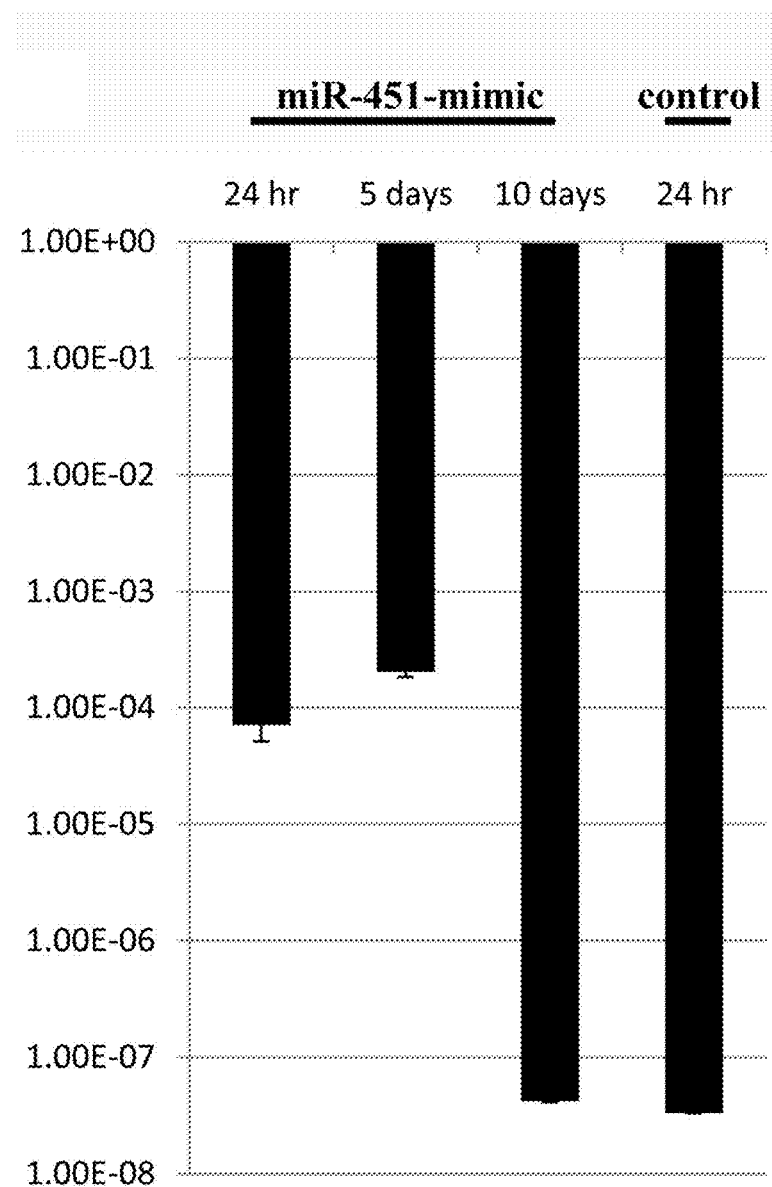
FIGS. 4A-4C show that Hsa-miR-451 transfection decreases ALL cell growth in vivo.

As described herein, decreased expression of miR-451 in comparison to a control level can serve as a prognostic factor for ALL relapse risk, as low expression of miR-451 at diagnosis predict worse outcome. To demonstrate the effect of miR-451 in ALL, miR-451 was up regulated in ALL derived Nalm-6 cell line using miR-451 mimic (SEQ ID NO: 2) transfection (Nalm-6/miR-451) by electroporation (Amaxa Nucleufector technology; kit T; program c-005). RQ-PCR was used to confirm miR-451 expression in the transfected cells. The RQ-PCR results showed a significant increase in the expression of miR-451 in Nalm-6/miR-451 versus the negative control cells (control) (FIG. 4A).

Figure 4B:
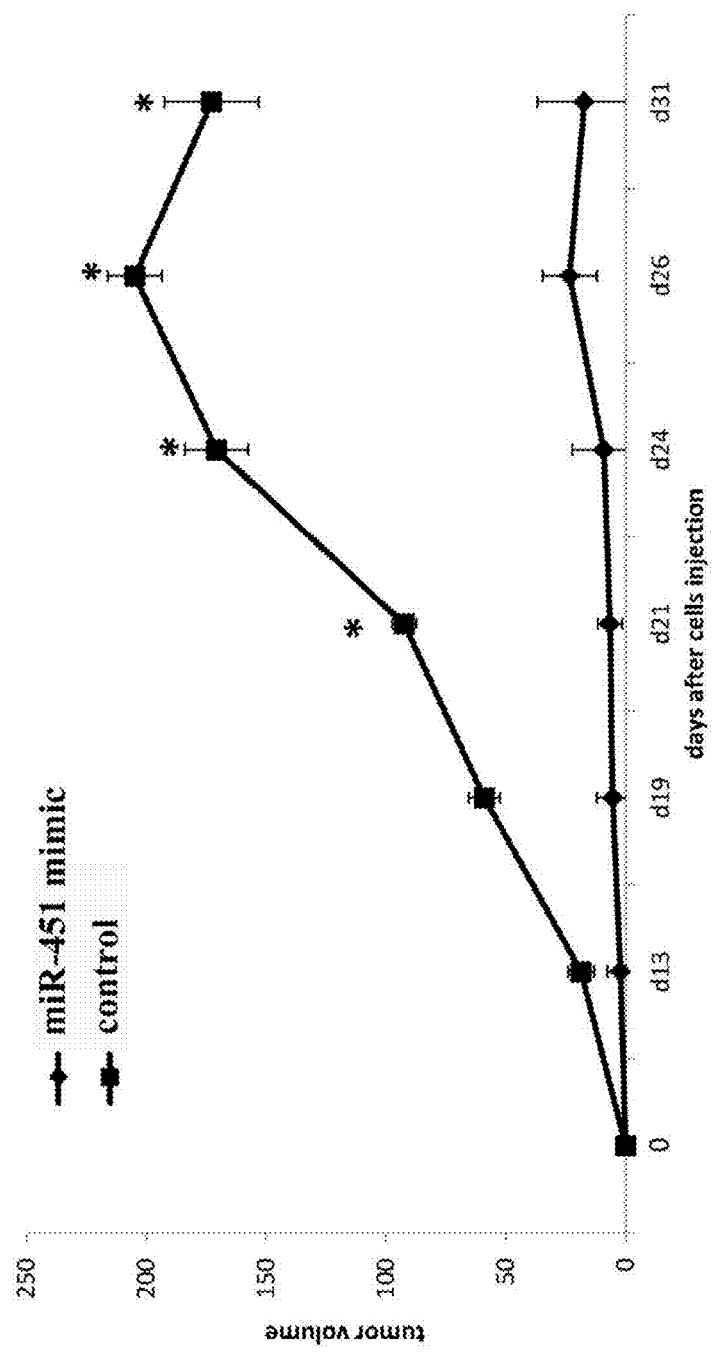
Figure 4C:
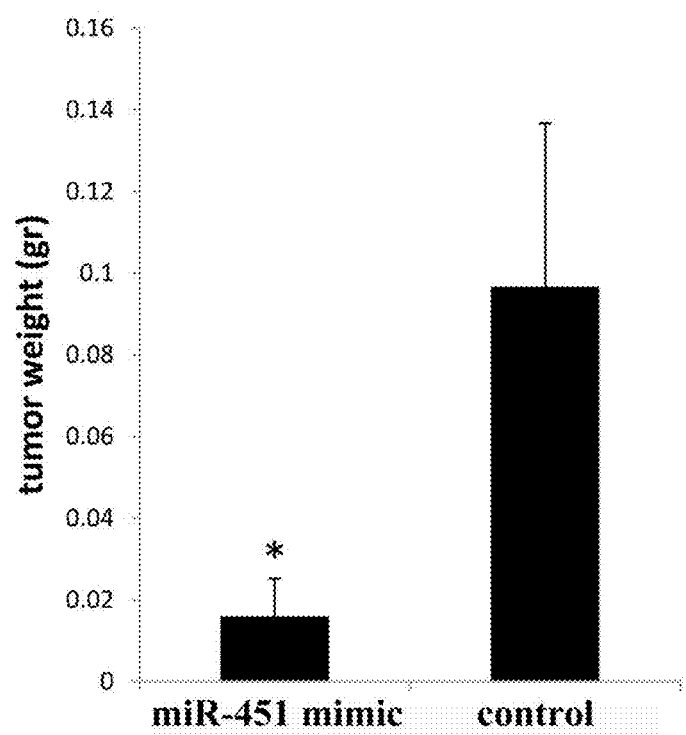

To further study the putative tumor-suppressive function of hsa-miR-451 in vivo, $10^7$ viable Nalm-6 untransfected cells, transfected in vitro with miR-451, or transfected with scrambled control nucleic acid, were injected s.c. into the right flanks of 6-week-old female NOD/SCID mice. Whereas animals transplanted with scrambled miR control cells developed large tumors after 20 days, animals receiving Nalm-6/miR-451 cells showed significantly decreased tumor growth (FIG. 4B). On day 26, the median tumor volume in the scrambled control mice and the miR-451 mice were 204.69 mm$^3$ (SE=63.96) and 23.32 mm$^3$ (SE=13.12) respectively (P=0.019). At the end of the experiment mice were sacrificed and the tumors were weighted. The median tumor weight in the scrambled control mice and the miR-451 mice were 0.0966 gr (SE=0.040) and 0.0159 gr (SE=0.0009) respectively (P=0.046) (FIG. 4C). These results indicate that up regulation of hsa-miR-451 mediates cell growth in ALL and supports the role of hsa-miR-451 as a tumor suppressor gene.

Example 4: miR-451 Inhibits NAMPT Expression by Targeting NAMPT 3'-UTR in ALL Cell Lines This example demonstrates that the NAMPT mRNA is a specific target of miR-451 translation inhibition, Using open access software programs (TargetScan and miRanda), nicotinamide phosphoribosyltransferase (NAMPT) was identified as a predicted target of miR-451.

Figure 5A:
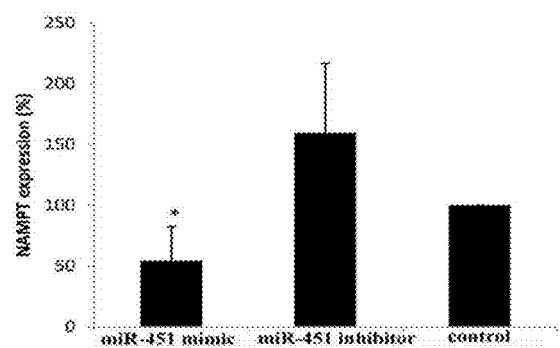
FIGS. 5A-5B show the effect of miR-451 on NAMPT expression.

To determine the effects of miR-451 on NAMPT expression, Nalm-6 cells were transfected with miR-451 mimic (SEQ ID NO: 2) and miR-451 inhibitor (GeneCopoeia miArrest miR-451, an inhibitor expression clone) and NAMPT expression was measured by FACS analysis using a specific NAMPT antibody. Following the over-expression of miR-451 in cells, NAMPT protein expression was decreased by 46% of NAMPT while miR-451 inhibitor caused a 60% increase in NAMPT expression in Nalm-6/miR-451 cells (FIG. 5a, P<0.05).

Figure 5B:
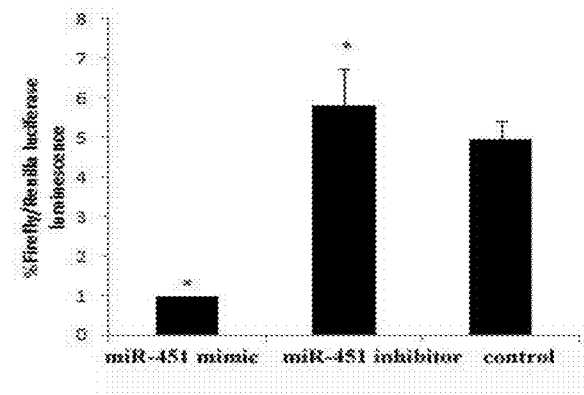

To confirm that NAMPT is a direct target of miR-451, luciferase reporter vectors were generated that contained the NAMPT 3'-UTR (LightSwitch NAMPT 3'UTR Reporter GoClone). Luciferase reporter assays (LightSwitch Luciferase Assay; SwitchGear) were then performed in the presence and absence of miR-451mimic and inhibitor to determine whether NAMPT was a direct downstream target of miR-451. The relative luciferase activity of the reporter that contained NAMPT 3'-UTR was decreased in 80% when miR-451 mimics were transfected. In contrast, miR-451 inhibitor showed a significant 17% increase in the relative luciferase activity of the reporter (FIG. 5B, P<0.05). These results confirm that that miR-451 directly binds the 3'-UTR of NAMPT transcript, and negatively regulating its protein levels.

Figure 6A:
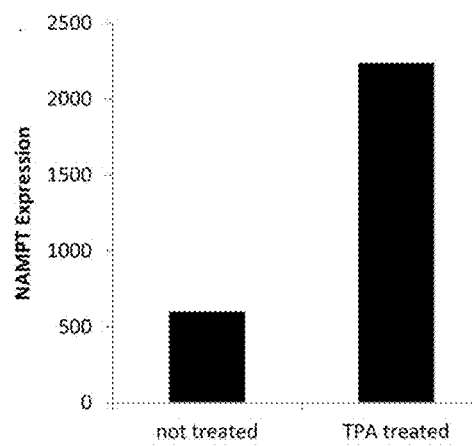
FIGS. 6A-6B show the effect of NAMPT expression on NAD levels.

Studies by several investigators have shown that 12-0-tetradecanoylphorbol-13-acetate (TPA) (Sigma) is an extraordinarily potent tumor promoter and stimulates protein kinase C (PKC). Since NAMPT is over-expressed in several tumors, it was believed that it might be possible to achieve NAMPT stimulation by TPA treatment. To test this hypothesis. Peripheral blood cells were treated with 50 ng/ml TPA for 24 hours and NAMPT expression was measured by FACS using a specific NAMPT antibody. Cells treated with TPA showed an increase of more than 4 folds in NAMPT expression levels (FIG. 6A).

Figure 6B:
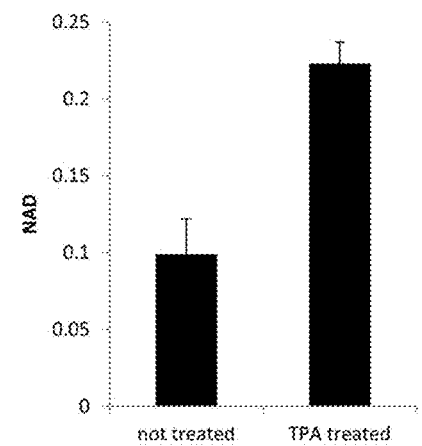

NAMPT is the rate-limiting enzyme in the $NAD^+$ biosynthetic pathway. Thus, $NAD^+$ levels in the stimulated cells were measured using a standard $NAD^+$ assay (Biovision NADH/NAD Quantification Kit). It was found that the cellular $NAD^+$ levels in the TPA stimulated cells were 2 fold higher (FIG. 6B).

Example 5: Increased Expression of NAMPT Increases Sensitivity of ALL Cells to the NAMPT Inhibitor, FK866

Example 4 shows that miR-451 regulates NAMPT expression, and by extension, cellular $NAD^+$ levels. This example demonstrates that ALL cells in which miR-451 expression is decreased have increased sensitivity to the NAMPT inhibitor FK866.

FK866 is a potent NAMPT inhibitor that is known to cause the depletion of intracellular $NAD^+$ levels in the cells and ultimately induces apoptosis. The effect of FK866 treatment in Nalm-6 cell line on apoptosis and $NAD^+$ levels was thus characterized.

Figure 7A:
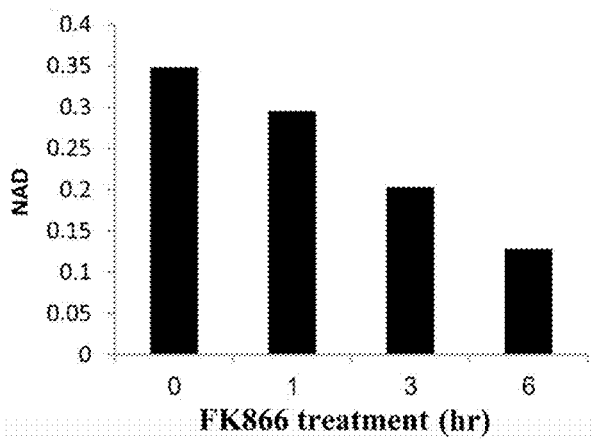
FIGS. 7A-7B show that NAMPT inhibitor FK866 induced apoptosis and reduction in NAD levels in NALM-6 cells.
Figure 7B:
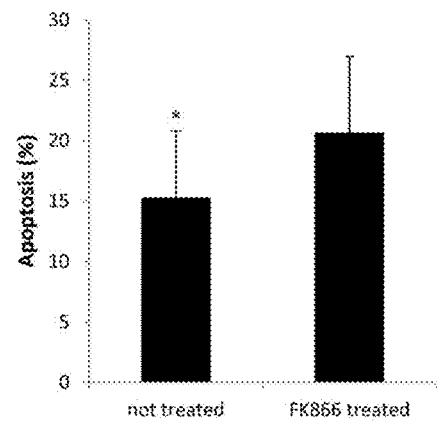

Nalm-6 cells were treated for 1, 3, and 6 hours with 1 nM FK866 (Sigma) and $NAD^+$ formation was measured using NAD assay as described. The results show a gradual decrease in $NAD^+$ detection following FK866 treatment (FIG. 7A). Hence, FK866 is a specific inhibitor of $NAD^+$ formation in Nalm-6 cell line. To measure the effect of $NAD^+$ depletion following FK866 treatment on Nalm-6 cells, apoptosis and viability were measured. Nalm-6 cells were treated for 48 hours with 1 nM FK866 and apoptosis was measured using FACS. As shown in FIG. 7, FK866 both potently inhibited $NAD^+$ formation (FIG. 7A) and induced apoptosis of Nalm-6 cells (FIG. 7B).

Figure 8A:
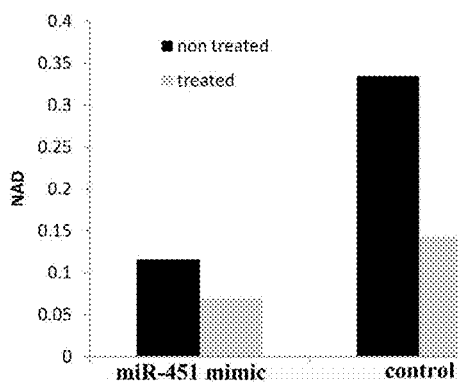
FIGS. 8A-8B show sensitivity of ALL cell line to NAMPT inhibitor, FK866. NAD levels were measured using NAD assay in cells treated for 3 hours with FK866. Assayed cells were transfected with miR-451 mimic (FIG. 8A), inhibitor (FIG. 8B), or scrambled negative control (representative figure of one experiment).
Figure 8B:
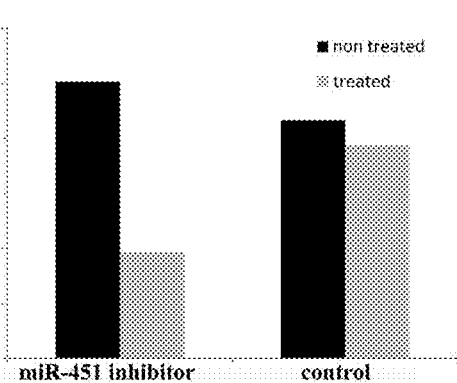

The sensitivity of NALM-6 cells to the NAMPT inhibitor FK866 was measured in cells following transfection with miR-451 mimic or miR-451 inhibitor (FIG. 8). The sensitivity was measured by levels of $NAD^+$. Nalm-6/miR-451 cells showed less change in NAD+ production after FK866 treatment compared to Nalm-6/miR-NC (FIG. 8A). However, Nalm-6/miR-inhibitor cells showed more than 5 fold change in NAD+ production after FK866 treatment compared to Nalm-6/miR-NC (FIG. 8B; p=0.003). These results suggest that ALL cells expressing low levels of miR-451 are more sensitive to NAMPT inhibitors. Thus, miR-451 expression can distinguish between patients that could benefit from treatment with NAMPT inhibitors, such as FK866.

Example 6: miR-1290 Targets Expression of SOCS4

This example describes the determination of SOCS4 as a target of miR-1290, and which will be affected by the miR-1290 overexpression observed in ALL subjects with a higher rate of relapse.

Using target prediction softwares (miRDB, miRANDA), SOCS4 was chosen as a potential target of miR-1290. The Socs4 gene encodes a member of the STAT-induced STAT inhibitor (SSI), also known as suppressor of cytokine signaling (SOCS), family SSI family members are cytokine-inducible negative regulators of cytokine signaling. SOCS4 negatively regulates the STAT family. The expression of this gene is induced by various cytokines, including IL6, IL10, and interferon (IFN)-gamma. The protein encoded by this gene can bind to JAK kinase, and inhibit the activity of JAK kinase. The JAK kinase in known to be activated in leukemia.

Figure 9:
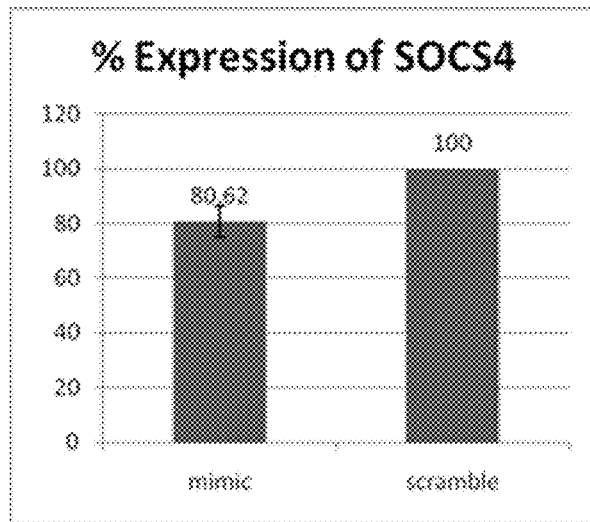
FIG. 9 shows SOCS4 protein expression levels following the over-expression of miR-1290 (mimic) in comparison to control (scramble). Protein expression was determined and quantified by Western blotting.

Following transfection of miR-1290 mimic (SEQ ID NO: 4, over-expression), miR-1290 inhibitor (SEQ ID NO: 5, silencing), and miR-scramble (control), into the Nalm6 cell line, the protein levels of SOCS4 were measured using Western blotting (p=0.029; FIG. 9). The values shown in the figure are mean±S.D from 3 experiments.

Figure 10A:
FIGS. 10A-10B show SOCS4 protein levels in ALL BM samples with high and low miR-1290 levels. Representative Western blot and (FIG. 10A) and quantitation (FIG. 10B) are shown.
Figure 10B:
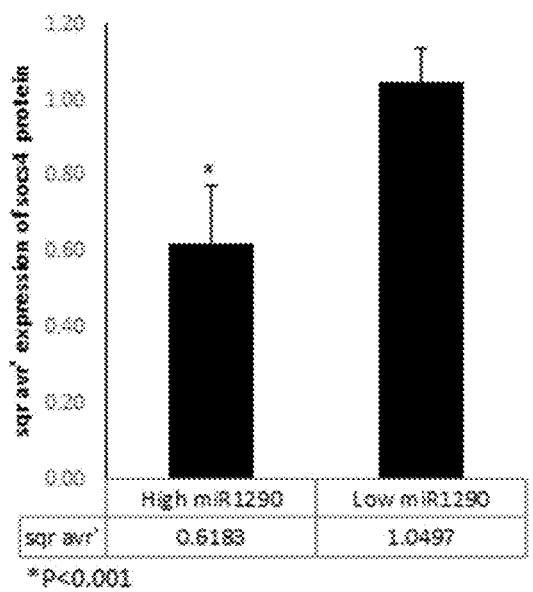

Additionally, SOCS4 protein levels were measured in 31 BM samples of ALL patients and compared to the levels of miR-1290. SOCS4 protein levels were significantly reduced in the samples harboring high miR-1290 expression levels (p<0.0001; FIG. 10).

Figure 11:
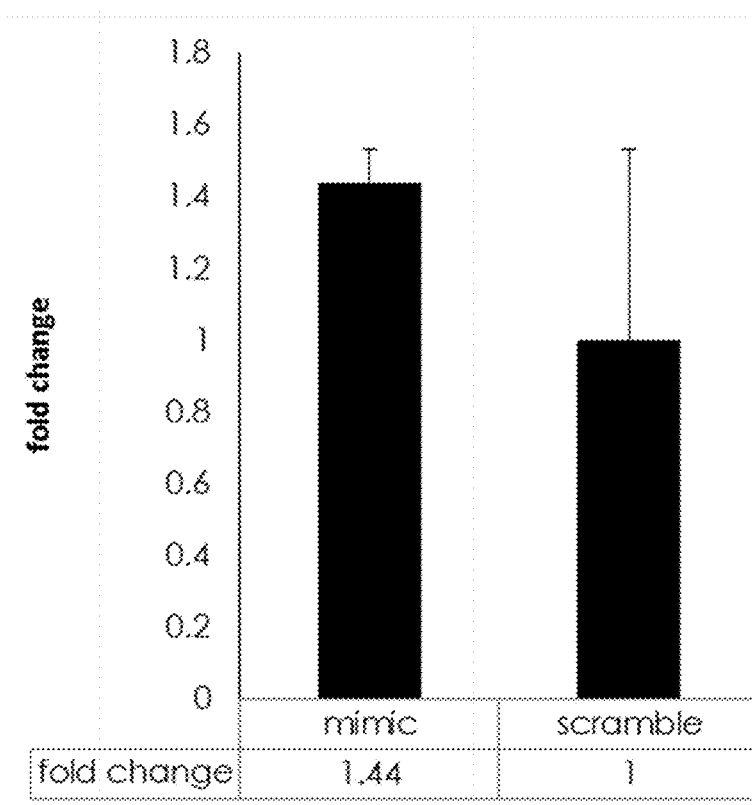
FIG. 11 shows a quantitation of phosphorylated-STAT5 protein levels following overexpression of miR-1290 (mimic).

Phosphorylated STAT5 (phospho-STAT5) levels were measured by FACS analysis following transfection of miR-1290 mimic (overexpression) into NALM-6 cell line. An increase of 50% in the levels of pSTAT5 protein is evident in the cells expressing high levels of miR-1290 (FIG. 11).

JAK2 is an essential gene in the leukemic process. We have shown that the over-expression of miR-1290 results in the down-regulation of SOCS4. SOCS4 normally inhibits the activity of JAK2, thus its down-regulation results in the increase activity of JAK2, with no need in external signals (as cytokines).

This result suggests that the expression levels of miR-1290 may predict the presence or absence of an activated JAK/STAT pathway, and predict who may benefit from JAK2 inhibitors.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method for treatment of relapse of acute lymphoblastic leukemia (ALL) in a subject that has been diagnosed with ALL, comprising:
   detecting the expression level of miR-1290 or miR-1290 and miR-451 in a sample from the subject; and
   determining that the subject has an increased risk of ALL relapse if the expression level of miR-1290 is statistically significantly increased in comparison with a control expression level of miR-1290, or the expression level of miR-1290 is statistically significantly increased and the expression level of miR-451 is statistically significantly decreased in the subject in comparison to the control expression levels of miR-1290 and miR-451; and
   administering to the subject an ALL treatment comprising a NAMPT and/or JAK2 inhibitor.

2. The method of claim 1, wherein the control expression of miR-1290 or miR-1290 and miR-451 is a cutoff value.

3. The method of claim 1, wherein the risk of ALL relapse in the subject is further indicated by ALL-associated clinical criteria selected from the group consisting of: B-ALL and T-ALL diagnosis, minimal residual disease (MRD) high and low risk definitions, response to prednisone on day 8 of treatment; BFM high and low risk definitions, white blood count (WBC) being over or below 20,000 cells/ml, patient age being over one and under six years old or otherwise, COG high and standard risk definitions for induction therapy, COG low/average/high/very high risk definitions for post-induction therapy, and gender.

4. The method of claim 1, wherein the subject has been diagnosed with B-ALL.

5. The method of claim 1, wherein the sample is isolated from bone marrow or blood of the subject.

6. The method of claim 1, wherein the method is repeated at least once after the initiation of ALL therapy, and wherein a change in risk of ALL relapse is thereby monitored.

7. A system for treatment of relapse of acute lymphoblastic leukemia (ALL) in a subject that has been diagnosed with ALL comprising:
   detecting the expression level of miR-1290 in a sample from the subject;
   determining that the subject has an increased risk of ALL relapse if the expression level of miR-1290 is statistically significantly increased in comparison with a control expression level of miR-1290; and
   administering to the patient an ALL treatment comprising a NAMPT and/or JAK2 inhibitor.

8. A system for treatment of relapse of acute lymphoblastic leukemia (ALL) in a subject diagnosed with ALL comprising:
   detecting the expression level of miR-1290 and at least one of miR-151-5p and miR-451 in a sample from the subject; and
   determining that the subject has an increased risk of ALL relapse if the expression level of miR-1290 is statistically significantly increased in comparison with a control expression level of miR-1290, combined with a statistically significant decrease in the expression of at least one of miR-151-5p and miR-451 in comparison to the control expression of miR-151-5p and/or miR-451; and
   administering to the subject an ALL treatment comprising a NAMPT and/or JAK2 inhibitor.

9. The system of claim 8, wherein the control expression of miR-1290 is a cutoff value.

10. The system of claim 9, wherein the control expression of miR-1290, miR-151-5p, and miR-451 are separate cutoff values.

11. The system of claim 8, wherein the risk of ALL relapse in the subject is further indicated by ALL-associated clinical criteria selected from the group consisting of: B-ALL and T-ALL diagnosis, minimal residual disease (MRD) high and low risk definitions, response to prednisone on day 8 of treatment; BFM high and low risk definitions, white blood count (WBC) being over or below 20,000 cells/ml, patient age being over one and under six years old or otherwise, CCG high and low risk definitions, and gender.

12. The system of claim 8, wherein the subject has been diagnosed with B-ALL.

13. The system of claim 8, wherein the sample is isolated from bone marrow or blood of the subject.

14. The system of claim 8, further comprising administering a composition comprising an anthracycline to the subject.

15. The system of claim 9, further comprising administering a composition comprising an anthracycline to the subject.

* * * * *